US009808168B2

(12) United States Patent
Goor et al.

(10) Patent No.: US 9,808,168 B2
(45) Date of Patent: *Nov. 7, 2017

(54) METHOD AND SYSTEM FOR NON-INVASIVE MEASUREMENT OF CARDIAC PARAMETERS

(71) Applicant: New N.I. Medical (2011) LTD., Petah Tikva (IL)

(72) Inventors: Daniel A. Goor, Tel Aviv (IL); Efim Frinerman, Bat Yam (IL); Evgeny Granov, Ra'anana (IL); Igor Granov, Raanana (IL)

(73) Assignee: New N.I. Medical (2011) LTD., Petah Tikva (IL)

( * ) Notice: Subject to any disclaimer, the term of this patent is extended or adjusted under 35 U.S.C. 154(b) by 96 days.

This patent is subject to a terminal disclaimer.

(21) Appl. No.: 14/543,114

(22) Filed: Nov. 17, 2014

(65) Prior Publication Data

US 2015/0073250 A1    Mar. 12, 2015

Related U.S. Application Data

(63) Continuation of application No. 12/439,985, filed as application No. PCT/IL2007/001088 on Sep. 4, 2007, now Pat. No. 8,911,379.

(Continued)

(51) Int. Cl.
*A61B 5/02* (2006.01)
*A61B 5/04* (2006.01)
(Continued)

(52) U.S. Cl.
CPC .......... *A61B 5/04012* (2013.01); *A61B 5/021* (2013.01); *A61B 5/0205* (2013.01);
(Continued)

(58) Field of Classification Search
None
See application file for complete search history.

(56) References Cited

U.S. PATENT DOCUMENTS

| 3,340,867 A | 9/1967 | Kubicek et al. |
| 4,429,701 A | 2/1984 | Goor et al. |

(Continued)

OTHER PUBLICATIONS

Nieminen M. S., "Pharmacological options for acute heart failure syndromes: Current treatments and unmet needs", Eur Heart J 2005; 7(Suppl B):20-24.

(Continued)

*Primary Examiner* — Michael Carey
*Assistant Examiner* — Elizabeth K So
(74) *Attorney, Agent, or Firm* — Wiggin and Dana LLP; Gregory S. Rosenblatt; Andrew D. Bochner (57) ABSTRACT

A method and system are presented for use in assessment of at least one cardiac parameter of an individual. An electrodes arrangement is applied to an individual's body, for applying an electrical field to the body and providing an electrical output indicative of a systolic impedance change and of a velocity of said change during a cardiac cycle. Also provided is additional data indicative of at least of the following conditions of the individual: a value of total peripheral resistance (TPR), a value of cardiac index (CI), and existence of the AHF condition. Data corresponding to these condition is analyzed to determine whether the TPR satisfies a first predetermined condition and/or the CI satisfies a predetermined second condition and/or whether the acute heart failure (AHF) condition is identified, to thereby use the data indicative of the measured electrical output and selectively calculate said at least one cardiac parameter based on either the systolic impedance change data or on said data of the velocity of the impedance change.

20 Claims, 7 Drawing Sheets

Related U.S. Application Data (60) Provisional application No. 60/842,035, filed on Sep. 5, 2006.

(51) Int. Cl.

| | | |
|---|---|---|
| *A61B 5/029* | (2006.01) | |
| *A61B 5/053* | (2006.01) | |
| *A61B 5/0205* | (2006.01) | |
| *A61B 5/021* | (2006.01) | |
| *A61B 5/0408* | (2006.01) | |
| *A61B 5/0432* | (2006.01) | |
| *A61B 5/044* | (2006.01) | |
| *A61B 5/0295* | (2006.01) | |
| *A61B 5/024* | (2006.01) | |

(52) U.S. Cl.
CPC .......... *A61B 5/029* (2013.01); *A61B 5/02028* (2013.01); *A61B 5/02035* (2013.01); *A61B 5/0295* (2013.01); *A61B 5/044* (2013.01); *A61B 5/0408* (2013.01); *A61B 5/04011* (2013.01); *A61B 5/0432* (2013.01); *A61B 5/053* (2013.01); *A61B 5/024* (2013.01)

(56) References Cited

U.S. PATENT DOCUMENTS

| | | | |
|---|---|---|---|
| 4,895,163 | A | 1/1990 | Libke et al. |
| 5,469,859 | A | 11/1995 | Tsoglin et al. |
| 5,735,284 | A | 4/1998 | Tsoglin et al. |
| 6,102,869 | A | 8/2000 | Meier et al. |
| 6,158,438 | A | 12/2000 | Shen |
| 6,228,033 | B1 | 5/2001 | Koobi et al. |
| 6,339,722 | B1 | 1/2002 | Heethaar et al. |
| 6,511,438 | B2 | 1/2003 | Bernstein et al. |
| 6,615,077 | B1 | 9/2003 | Zhu et al. |
| 2005/0043895 | A1* | 2/2005 | Schechter .......... A61B 5/02028 702/19 |
| 2005/0090753 | A1 | 4/2005 | Goor et al. |
| 2006/0111641 | A1 | 5/2006 | Manera et al. |

OTHER PUBLICATIONS

Schmidt C. et al., "Comparison of electrical velocimetry and transoesophageal Doppler echocardiography for measuring stroke volume and cardiac output", British Journal of Anaesthesia 2005; 95, 603-10.
Cohen A. J. et al., "Non-invasive measurement of cardiac output during coronary artery bypass grafting", Eur J Cardiothorac Surg 1998; 14:64-9.
Bernstein D. P. et al., "Stroke volume equation for impedance cardiography", Medical & Biological Engineering & Computing 2005; 43, 443-50.
Bonjer F. H. et al., "The origin of the variations of body impedance occurring during the cardiac cycle", Circulation 1952; 6: 415-20.
Cotter G. et al., "Accurate, noninvasive continuous monitoring of cardiac output by whole-body electrical bioimpedance", Chest. Apr. 2004;125(4):1431-40.
Cotter G. et al., "Impedance cardiography revisited", Physiol. Meas., 2006, 27:817-827.
Handelsman H., "Measuring Cardiac Output by Electrical Bioimpedance", Health Technology Assessment Reports, US Dept Health and Human Services, Public Agency for Health Care Policy and Research 1991; 6:1-13.
Koobi T. et al., "Cardiac output can be reliably measured noninvasively after coronary artery bypass grafting operation", Crit Care Med 1999; 27:2206-11.
Kubicek et al., "The Minnesota impedance cardiograph", Biomed. Eng. 1974, 9:410-16.
Kushner R. F. et al., "Estimation of total body water by bioelectrical impedance analysis", Am J Clin Nutr 1986; 44: 417-24.
Moshkovitz Y. et al., "Recent developments in cardiac output determination by bioimpedance: comparison with invasive cardiac output and potential cardiovascular applications", Curr Opin Cardiol. May 2004;19(3):229-37.
Ninomiya M. et al., "Physical properties of flowing blood", Biorheology, 1988, 25(1-2):319-28.
Patterson et al., "Development of an Electrical Impedance Plethysmograph System to Monitor Cardiac Output", Proc. 1st Annu Rocky Mt. Bioeng. Sympos., 1964, 56-71.
Raaijmakers et al., "A Meta-analysis of Published Studies Concerning the Validity of Thoracic Impedance Cardiograph", Ann NY Acad Sci 1999; 873:121-34.
Shankar T. M. R. et al., "The contribution of vessel volume changes and blood resistivity change to the electrical impedance pulse", IEEE Biomed Eng BME-32, #3:192-198, Mar. 1985.
Tischenko M. I., "Estimation of Stroke volume by Integral Rheogram of the Human Body", Sechenov Phisiological J 1973; 59:1216-24.
Visser K. R., "Electric properties of flowing blood and impedance cardiography", Ann Biomed Eng 1989; 17:463-73.
Visser K. R. et al., "Impedance cardiography and electrical properties of blood", Proceedings of the Vth ICEBI, Aug. 1981, Tokyo, pp. 13-16.
Visser K. R. et al., "Investigation of the origin of the impedance cardiogram by means of exchange transfusion with stroma free haemoglobin solution in the dog", Cardiovasc Res. Jan. 1990; 24(1):24-32.
Wtorek J. et al., "Relations between components of impedance cardiogram analyzed by means of finite element model and sensitivity theorem", Annals of Biomedical Engineering 2000; 28, 1352-61.
International Search Report and Written Opinion from International Application No. PCT/IL2007/001088, dated Sep. 22, 2008.
International Preliminary Report on Patentability from International Application No. PCT/IL2007/001088, dated Apr. 7, 2009.

\* cited by examiner

METHOD AND SYSTEM FOR NON-INVASIVE MEASUREMENT OF CARDIAC PARAMETERS

CROSS REFERENCE TO RELATED APPLICATIONS

This application is a continuation of prior U.S. patent application Ser. No. 12/439,985 (now U.S. Pat. No. 8,911,379), filed Oct. 29, 2009, which is a 371 National Stage of International Application Number PCT/IL2007/001088, filed Sep. 4, 2007, which in turn claims the benefit under 35 USC 119(e) of U.S. Provisional Application No. 60/842,025, filed on Sep. 5, 2006, all of which are incorporated herein by reference in their entirety.

FIELD OF THE INVENTION

The present invention is generally in the field of cardiology. More specifically, the invention concerns non-invasive techniques for measuring and monitoring the main hemodynamic parameters of a patient, such as cardiac parameters, utilizing body bioimpedance techniques.

BACKGROUND OF THE INVENTION

Measurement of cardiac output is a basic diagnostic and therapeutic requirement in the management of patients with cardiac conditions. There are three widely accepted methods which accurately measure cardiac output, and they are therefore recognized as standard methods and serve as gold-standard methods for the evaluation of new technologies for cardiac output measurement. These include the direct Fick's principles based parameters (the rate of diffusion is proportional to the difference in concentration, accordingly, the volume of oxygen consumed per unit time is proportional to the difference in oxygen content between arterial and venous blood, with the degree of proportionality depending on the volume of blood pumped per unit time), dye dilution, and bolus thermodilution. All these methods measure the rate of dilution of a known volume indicator. The indicator for Fick is oxygen, thermodilution uses cold saline or dextrose, dye dilution uses cardiogreen, and they are all invasive techniques that require specialist expertise and expensive capital equipment, can be employed only on hospital premises, and all pose a certain risk.

The development of non-invasive alternative methods is of great practical value.

Currently, two technologies are accepted in clinical settings for non-invasive measurement of cardiac output. These are Doppler Echocardiography and Impedance Cardiography methods. Although the Doppler echocardiography technique is reliable, both techniques require expensive equipment and specialist expertise.

Three basic technologies exist for measuring cardiac output by electrical bioimpedance:

(A) Thoracic Impedance Cardiography (TIC).

According to this technique, electrodes are applied to the root of the neck and to the lower part of the thorax, and the chest is measured as an electrical field. The method was first suggested in 1964 [Patterson et al., Proc. 1$^{st}$ Annu Rocky Mt. Bioeng. Sympos., 1964, 56-71] and was upgraded in 1974 [Kubicek et al. Biomed. Eng. 1974, 9:410-16] where the $\Delta R$ parameter was replaced by its first derivative, the dR/dt, of the impedance change, multiplied by the ejection time (T), for the stroke volume calculation. Subsequently, a number of variations in the variables of the formula were offered, but the TIC cardiac output results remained inaccurate in patients with cardiac conditions (Handelsman H, Health Technology Assessment Reports, US Dept Health and Human Services, Public Agency for Health Care Policy and Research 1991; 6:1-13; Raaijmakers et al, Ann NY Acad Sci 1999; 873:121-34).

The sources of errors in TIC established by experimental and clinical data include the following: (1) individual anatomical differences in the position of organs in the thorax cage; (2) non-linear changes of the electrical resistivity of the flowing blood; (3) the current electrodes position and the distance between the voltage electrodes; (4) the ejection pattern; (5) the outflow problem; (6) the influences of multifactors on the thoracic basal impedance value; (7) the inability to assess the contribution from the right heart and pulmonary circulation; and (8) the inability to assess impedance changes independently of volume changes, such as mechanical displacements of the heart and great vessels.

(B) Whole Body ICG ($ICG_{WB}$)

According to this technique, tetrapolar electrodes are applied to all four limbs. The method was suggested in 1973 by Tischenko [Sechenov Phisiological J 1973; 59:1216-24)], and is currently promoted by Koobi et al., Crit Care Med 1999; 27:2206-11.

In many conditions, the accuracy of the $ICG_{WB}$ technique is higher than that of the TIC due to the fact that the peripheral systolic impedance changes are more reliable signals for calculating the stroke volume than the thoracic systolic impedance waveforms. Nevertheless, this technology is cumbersome, and in many clinical conditions the extremities are used for invasive IV or IA procedures such as intra-arterial pressure monitoring, IV treatment, etc. Movement artifacts also increase due to the use of multiple electrodes. All these factors make it difficult or impractical to use these methods in clinical conditions.

(C) Regional Impedance Cardiography (RIC)

This technique utilizes two pairs of electrodes, one pair of electrodes being applied to one wrist and the other pair of electrodes—to the contralateral ankle. As an electrical field between the electrodes sites is a body region which consists of three segments—one arm, the trunk, and one leg, this method is called regional impedance cardiography (RIC). This technique was approbated in cardiac surgery clinics in 1998 by Cohen et al. [Eur J Cardiothorac Surg 1998; 14:64-9]; Cotter et al., Accurate, noninvasive continuous monitoring of cardiac output by whole-body electrical bioimpedance, Chest. 2004 April; 125(4): 1431-40; Cotter et al, Impedance cardiography revisited. Physiol. Meas., 2006, 27:817-827. Compared to TIC, the accuracy of RIC is higher by a factor of 2.

SUMMARY OF THE INVENTION

There is a need in the art to facilitate non-invasive techniques for measuring and monitoring the main hemodynamic parameters of a patient, such as cardiac parameters, utilizing body bioimpedance techniques. This is associated with the following. Although, as indicated above, RIC provides for increasing the accuracy of measurement by a factor of 2, it appears that this technique is not acceptable for a significant group of patients, approximately 15% (Cotter et al, Impedance cardiography revisited. Physiol. Meas., 2006, 27:817-827).

The present invention provides a solution for the above, and is based on the understanding of the well-established biophysical and physiological data of the interaction of the conductivity changes of the flowing blood with electrical resistance changes caused by the arterial wall expansion during the cardiac cycle (Ninomiya M, et al, Physical properties of flowing blood. Biorheology, 1988, 25(1-2): 319-28; Visser et al, Impedance cardiography and electrical properties of blood, Proceedings of the Vth ICEBI, August 1981, Tokyo, pp. 13-16; Investigation of the origin of the impedance cardiogram by means of exchange transfusion with stroma free haemoglobin solution in the dog. Cardiovasc Res. 1990, January 24(1):24-32; Wtorek et al, Relations between components of impedance cardiogram analyzed by means of finite element model and sensitivity theorem. Annals of Biomedical Engineering 2000; 28, 1352-61).

In accordance with these data, there are two principally different sources of the recorded impedance waveform. The first source is conductivity changes due to volumetric changes of blood in the systolic expansion of arterial system during the cardiac cycle. Volumetric changes are precisely assessed by the volume ($\Delta R$) wave. The second source is conductivity changes due to conductivity changes of the flowing blood caused by erythrocytes orientation effect during the cardiac cycle. Conductivity changes caused by the flowing blood are precisely assessed by the blood flow velocity (dR/dt) wave.

Consequently, there are two variations of the impedance signals: volumetric pulsatile changes ($\Delta R$), and velocimetric pulsatile changes (dR/dt). The genesis of the impedance $\Delta R$ is attributed to the volumetric expansion of the entire arterial tree (Cotter et al, Impedance cardiography revisited, Physiol Measurement 2006; 27:817-27). The genesis of the dR/dt is predominantly attributed to the changes in orientation of erythrocytes, the degree of which depend on the velocity of the arterial pulsatile blood flow (Visser K R. Electric properties of flowing blood and impedance cardiography. Ann Biomed Eng 1989; 17:463-73).

Until recently there was a link between each of the two formulae, with a specific electrode configuration; the dR/dt was utilized by technologies with thoracic impedance placement, whereas the $\Delta R$ was used by technologies with peripheral (limb) placement of the electrodes. Since it was known that in cardiac conditions the SV results of the thoracic ICG were unreliable, it was still unknown how much of the error could be attributed to the electrode placement, and how much could be attributed to the dR/dt formula. However, a recent report clarified that the $\Delta R$ and dR/dt have similar effiencies in SV calculation (Cotter et al. Impedance cardiography revisited, Physiol Measurement 2006; 27:817-27).

The inventors have recently discovered that to calculate the SV in patients with acute heart failure there is an advantage to the velocimetric formula. The reason for this is that in patients with acute heart failure there is an arterial peripheral vasoconstriction, with a reduction in the arterial wall distensibility (Nieminen M S, Pharmacological options for acute heart failure syndromes. Current treatments and unmet needs. Eur Heart J 2005; 7(Suppl B):20-24).

The inventors have found that under such circumstances, the volumetric formula underestimates thermodilution SV results. However, because of the compromised distensibility of the constricted arterial tree, the maintenance of the required SV is achieved by a compensatory increase in the velocity of the systolic blood flow, leading to the better suitability of the dR/dt algorithm for calculating the SV in patients with acute heart failure.

There is thus provided according to one broad aspect of the invention, a method for use in assessment of at least one cardiac parameter of an individual, the method comprising:

providing measured data indicative of a systolic impedance change, $\Delta R$, and of a velocity of said change, $\delta R/\delta t$, of an individual during a cardiac cycle;

providing data indicative of at least one of the following individual's parameters: total peripheral resistance (TPR) and cardiac index (CI);

analyzing said data indicative of at least one of such conditions of the individual as acute heart failure (AHF), TPR value and CI value to determine at least one of the following: whether the TPR satisfies a first predetermined condition, whether the CI satisfies a second predetermined condition, and whether the individual is under a condition wherein the individual is sustained by an AHF, to selectively calculate the at least one cardiac parameter based on either the systolic impedance change data or on the data of the velocity of the impedance change and generate output data indicative of the calculation results.

The measured data is obtained as an electrical output from an electrodes arrangement on an individual's body (individual's extremities): the electrodes arrangement is adapted to apply an electrical field to the body and to provide an electrical output indicative of change during a cardiac cycle.

In accordance with one embodiment of the invention, the method is performed using a tetrapolar electrode arrangement. Accordingly, said providing of the electrodes arrangement comprises attaching two electrode units on two limbs of the individual, preferably on one wrist and on a contralateral ankle (e.g. leg-arm).

According to one particular embodiment of the invention, the at least one cardiac parameter is selectively calculated based on the models utilizing two independent parameters, the $\Delta R/R$ volumetric parameter, and the $((dR/dt) \cdot T)$ blood velocity parameter, using separate equations. The latter may be those of the known Frinerman formula (see U.S. Pat. No. 5,469,859 assigned to the assignee of the present application) and Patterson equation, respectively, or new versions of the same corrected by the inventors, as will be described below. Each model is 'activated' according to the subject's individual conditions, i.e. in accordance with the TPR and/or the CI.

According to another embodiment, at least one cardiac parameter is selectively calculated based on a new combined approach (equation), according to which the calculation results are based either on the $\Delta R/R$ volumetric parameter, or the $((dR/dt) \cdot T)$ blood velocity parameter, in accordance with the TPR and/or CI and/or AHF condition of the individual.

The invention also provides an impedance measurement system for use in assessment of at least one cardiac parameter of an individual, the system comprising:

a measurement unit comprising an electrodes arrangement for attaching to the individual's extremities, said electrodes arrangement being adapted to apply an electrical field to the body and to provide an electrical output indicative of a systolic impedance change and of a velocity of said change during a cardiac cycle;

a control system connectable to the electrodes arrangement, the control system being preprogrammed to receive and analyze data indicative of the electrical output, based on at least one of such conditions of the individual as a value of total peripheral resistance (TPR), a value of cardiac index (CI), and an acute heart failure (AHF) condition, to thereby selectively calculate said at least one cardiac parameter based on the data of the velocity of the impedance change or on the systolic impedance change data if, respectively, at least one of the following conditions is satisfied or not: the TPR satisfies a predetermined first condition, the CI satisfies a predetermined second condition, and the AHF condition is identified.

The TPR data is calculated using the patient's blood pressure data BP and the measured systolic impedance change from the electrical output, where the cardiac output is calculated as a product of the measured stroke volume (calculated from the electrical output) and the heart rate, while the latter can be obtained form the ECG measurement or from the impedance wave. The CI is derived from the measured cardiac output as CI=(ΔR/R)/BSA, where BSA is the body surface area.

The invention also provides a control system for use with an impedance measurement system for assessment of at least one cardiac parameter of an individual, the control system comprising data input and output utilities and data processing and analyzing utility, and being configured and operable to: receive measured electrical output from an electrodes arrangement indicative of a systolic impedance change and of a velocity of said change during a cardiac cycle; determine at least one of the individual's total peripheral resistance (TPR), the individual's cardiac index (CI), and the existence of the AHF condition for identifying whether the TPR satisfies a first predetermined condition and/or the CI satisfies a second predetermined condition and/or the condition of AHF is identified; and process the measured electrical output by applying a predetermined model configured to selectively calculate said at least one cardiac parameter based on said data of the velocity of the impedance change or on the systolic impedance change data, if at least one of said conditions is satisfied or not, respectively.

BRIEF DESCRIPTION OF THE DRAWINGS

In order to understand the invention and to see how the same may be carried out in practice, some preferred embodiments will now be described, by way of non-limiting example only, with reference to the accompanying drawings, in which.

DESCRIPTION OF SOME EXEMPLARY EMBODIMENTS

Figure 1A:
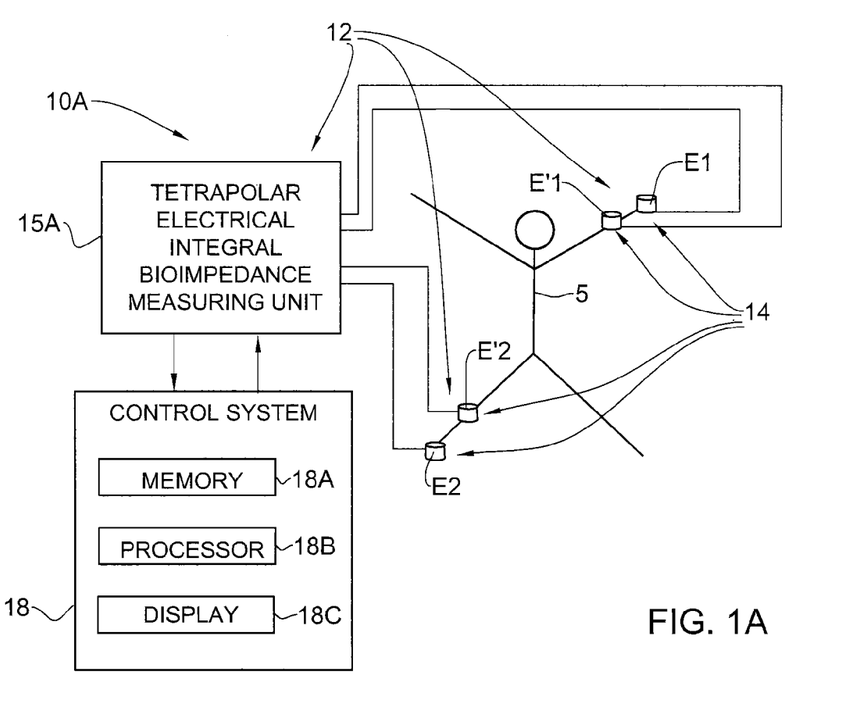
FIGS. 1A and 1B are schematic illustrations of the main constructional parts and operational principles of a measuring system according to one example of the invention utilizing the tetrapolar mode.

Referring to FIG. 1A, there is exemplified an impedance measurement system 10A of the present invention for use in assessment of at least one cardiac parameter of an individual (such as stroke volume, heart rate, cardiac output, cardiac index, etc.). Impedance measurement system 10A includes a measurement system 12 and a control system 18.

Measurement system 12 includes an electrodes' arrangement 14 for attaching to individual's 5 extremities, and an electrical integral bioimpedance measuring unit 15A. In the present example, system 10A is configured for the tetrapolar mode of operation. To this end, electrodes arrangement 14 is configured to define two pairs of electrodes, which in the present example is implemented by using four electrodes, $E_1$-$E_1'$ and $E_2$-$E_2'$ for applying a weak electrical current (e.g. about 0.5-2 mA, e.g. 1.4 mA) through the body and measuring an electrical output of the body. The electrical output is indicative of a systolic impedance change (volumetric change) and of a velocity of said change during a cardiac cycle. The first electrode unit $E_1$-$E_1'$ is applied to the patient's arm and the second electrode unit $E_2$-$E_2'$ is applied to the patient's leg. The electrodes are connected to electrical integral bioimpedance measuring unit 15A which is connectable (via wires or via wireless signal transmission) to control system 18.

Figure 1B:
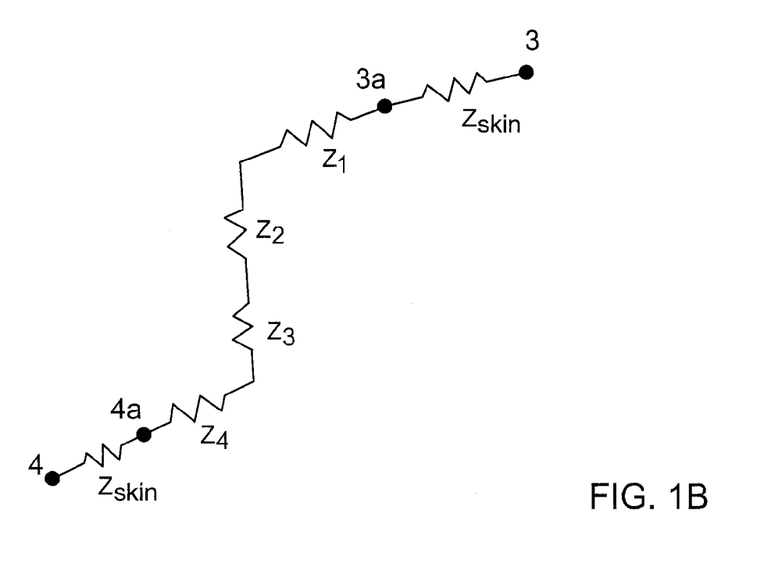

FIG. 1B shows an electrical scheme defined by the above configuration of the electrodes' arrangement. As shown, locations 3-3a and 4-4a of the two pairs of electrodes $E_1$-$E_1'$ and $E_2$-$E_2'$, respectively, define two impedance regions of the skin between the electrodes of each pair, $Z_{skin}$, and the body impedance regions $Z_1$, $Z_2$, $Z_3$ and $Z_4$.

Figure 2A:
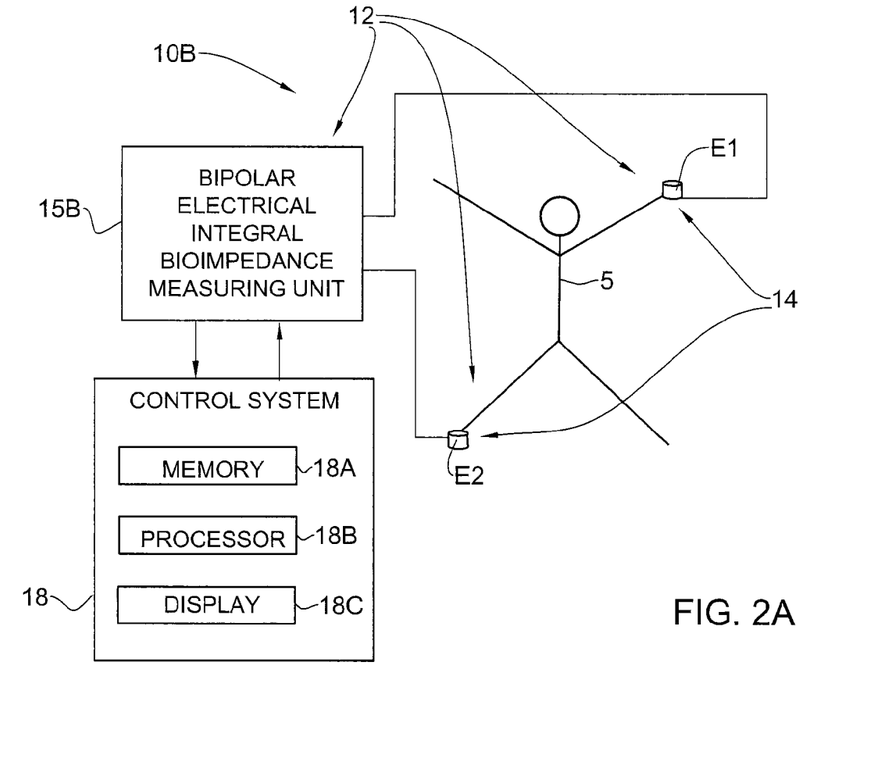
FIGS. 2A and 2B are schematic illustrations of the main construction parts and operational principles of a measuring system according to another example of the invention utilizing the bipolar mode.
Figure 2B:
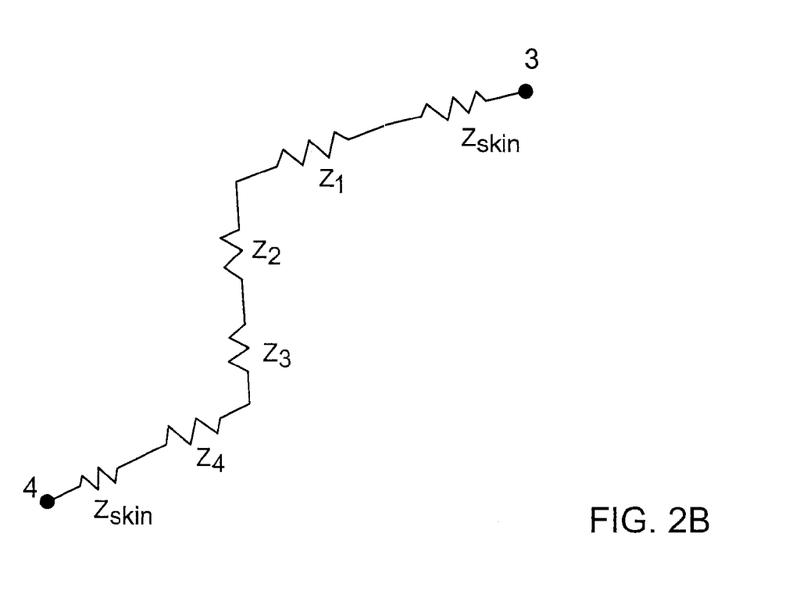

FIGS. 2A and 2B illustrate, respectively, an example of a measurement system 10B configured for the bipolar mode of operation utilizing an electrical integral bioimpedance measuring unit 15B, and an electrical scheme of such a system. To facilitate understanding, the same reference numerals are used for identifying components that are common in all the examples of the invention.

In both examples of FIGS. 1A-1B and 2A-2B, control system 18 is typically a computer system including inter alia data input and output utilities (not shown), memory utility 18A for storing reference data and a model data used for calculations, data processing and analyzing utility 18B, display 18C.

The control system is preprogrammed to analyze the detected signal (electrical output), according to the method of the present invention. The control system is adapted to calculate the TPR utilizing the patient's blood pressure data BP and the measured systolic impedance change from the electrical output. To this end, the control system calculates the cardiac output as a product of the measured stroke volume (calculated from the electrical output) and the heart rate. The latter can be obtained from the ECG measurement or from the impedance wave. The control system then operates to analyze the TPR data, for determining whether the TPR satisfies a first predetermined condition, to thereby apply a predetermined model configured to selectively calculate said at least one cardiac parameter based on either the volumetric change data or on the velocimetric impedance data. Output data indicative of the calculation results is then generated and presented (e.g. displayed).

The selective determination of the required parameter based on either the volumetric change data or on the velocimetric impedance data is associated with the following. The calculation of the left ventricular (LV) stroke volume (SV) by means of impedance cardiography (ICG) is based on two different physico-physiological principles, each of which can be independently used for measuring impedance changes of different origin which are incurred by the arterial pulsations.

The first physico-physiological principle is based on the volumetric changes. This principle uses an algorithm based on the electrical signal of the systolic impedance variation (SIV) generated by the increase of the intra-arterial pulse volume. The basic variable in the respective formula of this algorithm is ΔR/R, multiplied by outflow decay $(\alpha+\eta)/\beta$, where R is the value of basal resistance of the body (ohm), ΔR is the value of the SIV (Ohm), α and β are the systolic and diastolic time intervals, (α+β) being the time of a cardiac cycle, β being the descending part of the ΔR curve.

For this purpose, the following calculation modes can be used:

(1) Generally, the known Frinerman formula can be used (see U.S. Pat. No. 5,469,859 assigned to the assignee of the present application):

$$SV = \frac{Hct_{corr}}{K(\text{sex, age})} \cdot \frac{\Delta R}{R} \cdot \frac{H_{corr}^2}{R} \cdot \frac{\alpha + \beta}{\beta} \cdot K_{el} \cdot K_w \cdot IB \quad (1)$$

wherein:

$Hct_{corr}$ is the correcting factor depending from Hematocrit, being (145+0.35(Hct−40);

Hct is the Hematocrit level/value, obtained from the blood analysis of the individual;

$K_{sex, age}$ is the coefficient of the individual's body depending on the sex and age of the individual, and is determined as follows: (527.3−(3.1·(Actual Age-20))) for men younger than 20 years; 527.3 for men from 20 to 40 years; (527.3+(3.1·(Actual Age-40))) for men older than 40 years; (587.6−(2.9·(Actual Age-18))) for women younger than 18 years; 587.6 for women from 18 to 50 years; and (587.6+((2.9·(Actual Age-50))), for women older than 50 years;

H² corr is the corrected height of the patient, given by:

$$H_{corr} = (H_{real} + 2) \text{ if } \frac{\text{legs length}}{\text{body length}} = 0.66 \pm 0.04$$

or $$H_{corr} = (H_{real} - 2) \text{ if } \frac{\text{legs length}}{\text{body length}} = 0.54 \pm 0.04$$

or $$H_{corr} = (H_{real}) \text{ if } 0.62 \geq \frac{\text{legs length}}{\text{body length}} \geq 0.58$$

$K_{el}$ is the coefficient of electrolytic ions in the individual's blood, calculated based on the blood analysis and being given by: (a) for an individual exposed to a hemodialysis $$Kel = \frac{(Na^+ + K^+ + Mg^+ + Ca^+)(mmol/l)}{142 + 13(mmol/l)}$$

and (b) for other individuals $$Kel = \frac{(Na^+)(mmol/l)}{142(mmol/l)};$$

$K_w$ is the weight coefficient, being $$\frac{\text{Actual weight}}{\text{Ideal weight}^*}$$

for the corresponding sex and age of the individual according to the International Table of ideal weights; and IB is the index balance.

(2) Preferably, the corrected version of the above formula (1), proposed by the inventors, is used:

$$SV = \frac{\Delta R \cdot \rho \cdot L^2 \cdot (\alpha + \beta) \cdot KW \cdot HF}{R \cdot R_i \cdot \beta} \quad (2)$$

Here, ρ is the specific resistivity of blood (ohm/cm) being the value of the hematocrit, obtained from analysis of the individual's blood (Hct), L is the individual's height (cm), HF is the hydration factor related to the body water composition, $R_i$ is the resistance (ohm) corrected basal by the coefficient $K_{sex, age}$.

The inventors have introduced such a correction hydration factor in order to correct the influence of the hydration state on the reliability of the stroke volume measurements. The hydration factor HF is dependent on a ratio between the measured total body water (TBW) volume and the expected individual's normal water volume. The actual TBW is measured as (4.96+0.42 L²/R) for women and (8.30+0.42·L²/R) for men, where L is the individual's height and R is the measured resistance, and the TBW expected for the specific patient is typically determined as 40%-63% of the body weight for the specific patient. When the measured TBW is within a normal range, no correction is required, i.e. HF is set as 1.0. When a patient is dehydrated, which means that the measured TBW is below the above range, i.e. below 40% of the body weight, the SV would be decreased and thus needs to be corrected by the hydration factor, and similarly when the patient is over-hydrated, the measured TBW is higher than 63% of his weight, the SV would be increased and again needs to be corrected by the hydration factor. The hydration factor for such dehydrated and over-hydrated states is set as, respectively, $HF_1=TBW_{meas}/BL$, where $TBW_{meas}$ is the measured value of the patient's TBW and BL is the bottom limit of the normal TBW range, and $HF_1=TBW_{meas}/TL$ where TL is the top limit of the normal TBW range.

Thus, equations (1) and (2) differ from each other in that the coefficient $K_{sex\ age}$, which affects the basal resistance R, is represented in equation (2) by the corrected basal resistance $R_i$, and the IB (index balance) is represented in equation (2) by the hydration factor HF. The corrected height H²corr is not included in equation (2), but in patients whose arms are disproportionately long the electrodes should preferably be placed about 5 cm proximally to their regular position.

The invention utilizes the principal difference between the Hydration Factor and Index Balance consisting of the following: The hydration factor is the ΔR amplitude correction factor, while the index balance is used for assessment of patient's ideal R, prediction of which for extracellular body water included some irrelevant assumptions. The hydration factor is used only when the measured TBW for the specific patient is out of the normal range.

(3) The inventors have found that the above first physico-physiological principle (volumetric change based) can be further improved by using the following formula corrected by the inventors:

$$SV = \frac{\Delta R \cdot k_{HR} \cdot (\alpha + \beta)}{\beta} \cdot \rho \cdot \frac{L^2}{R \cdot R_i} \cdot KW \cdot HF \quad (3)$$

where $k_{HR}$ is a coefficient for correction of the (α+β)/β ratio where (α+β) is the duration of a cardiac cycle, being a sum of its anacrotic and catacrotic portion.

The $k_{HR}$ coefficient is set as follows: If the measured patient's heart rate $HR_{meas}$ is within the normal range, e.g. 60-100, then $k_{HR}=1$, if $HR_{meas}$ is less than the bottom limit BL of the normal range, then $k_{HR}=BL/HR_{meas}$ and if $HR_{meas}$ is higher than the top limit TL of the normal range, then $k_{HR}=TL/HR_{meas}$.

The second physico-physiological principle is the velocimetric principle. The essence of this principle is the fact that the electrical signal of the SIV is determined by the systolic changes of the arterial blood velocity. In this algorithm, the formula for the basic variable is dR/dt multiplied by the LV ejection time T.

To this end, generally the known Patterson equation $$sv = \frac{dR}{dt} \cdot T \cdot \rho \cdot \left(\frac{L}{R}\right)^2$$

might be used, but with corresponding calibration factor.

Preferably, however, the following equation, presenting a corrected version of the Patterson equation, proposed by the inventors, is used:

$$SV = k_{dr} \cdot \frac{dR}{dt} \cdot T \cdot \rho \cdot \left(\frac{L}{R}\right)^2 \quad (4a)$$

or a further corrected version:

$$SV = k_{dr} \cdot \frac{dR}{dt} \cdot T \cdot \rho \cdot \frac{L^2}{R \cdot R_i} \cdot KW \cdot HF \quad (4b)$$

wherein dR/dt is the peak of the first derivative of the blood resistance change during the cardiac cycle (ohm/sec), T is the cardiac ejection time (sec) namely the time interval between the point of the systolic upstroke of the maximal slope and the minimal point of the slope, and where the parameter D being a distance between the electrodes in the Patterson equation is replaced by the height L of the patient, and where a correcting coefficient $k_{dr}$ (calibration factor) to the expression ((dR/dt)·T) is added.

Currently, the volumetric algorithms are used in ICG technologies where electrodes are applied peripherally to the limbs, and the velocimetric formula is used in the thoracic approach, where electrodes are applied to the chest.

The inventors have found that the use of peripheral SIV signals is more accurate than that of thoracic SIV signals for calculating the stroke volume, and that in cases with normal values of total peripheral resistance (TPR) and of cardiac index (CI), the volumetric formula is preferable for measuring the SV, whereas in cases where TPR satisfies a first predetermined condition (is higher than a certain value within a range from about 1800 dynes/sec$^{-5}$ to about 1900 dynes/sec$^{-5}$), and preferably also when the CI satisfies a second predetermined condition (is lower than 2.5 lit/min/m$^2$), the velocimetric formula performs more accurately.

Thus, the control system (its processing and analyzing utility) analyzes the data indicative of the patient's TPR and preferably also the CI, and decides about the model to be used for the SV calculation. The model may include separate formulas for the first and second principles underlying the calculation, namely, either one of formulas (1), (2) and (3), or formula (4a) or (4b), respectively.

Alternatively, the model may include the following novel combined formula developed by the inventors with the appropriately adjusted coefficients in accordance with the TPR data and possibly also CI data:

$$SV = \left[\frac{\Delta R \cdot k_{HR} \cdot (\alpha + \beta)}{\beta} + k_{dr} \cdot \frac{dR}{dt} \cdot T\right] \cdot \rho \cdot \frac{L^2}{R \cdot R_i} \cdot KW \cdot k_{HF} \quad (5)$$

In the above model (5), either one of the following parameters $k_{HR}$ and $k_{dr}$ is selectively set to value 1 or 0 depending on at least the measured individual's TPR, as described above. It should be noted that in order to measure the TPR, the control system sets the coefficient $k_{dr}$ to 0, and thus calculates the stroke volume based on the volumetric changes, then calculates therefrom the cardiac output, utilizes this data and the blood pressure data to calculate the TPR. Then, the control system analyzes the TPR value and preferably also the cardiac index value to identify whether the predetermined condition(s) is/are satisfied or not to respectively set the coefficients $k_{HR}=0$ and $k_{dr}=1$ or vice versa.

The new formula (5) uses both of the electrical impedance waveform physiological sources, namely conductivity changes due to volumetric changes of blood in the arterial system during cardiac cycle assessed by the volume ($\Delta R$) wave, and conductivity changes due to conductivity changes of the flowing blood caused by erythrocytes orientation effect during the cardiac cycle assessed by the blood flow velocity (dR/dt) wave.

The technique of the present invention, based on the selective use of the appropriate calculation mode, is grounded on the peripheral displacement of the minimum two electrodes to the individual's body in a manner enabling the acquisition of electrical bioimpedance measurements of the regional part of an individual's body. Using this technique advantageously provides the current dispersion throughout an individual's/subject's/patient's body and extremities, to be reduced. The measured resistance of a part of an individual's/subject's/patient's body is increased in comparison with whole-body resistance, thus increasing the accuracy of the measured $R_0$ and $\Delta R$ and dR/dt. The other two extremities of the patient are free for other possible treatments or measurements, or for patient's activities. The one or two extremities with local pathology may be excluded. The technique provides for body water and segmental body water distribution assessment.

Thus, the present invention provides a novel system and method for calculating cardiac output through bioimpedance measurements of a patient. The system includes a bioimpedance measurement unit; electrodes' arrangement for attachment to a patient's arm and leg to provide an electrical output being in electrical communication with the resistance measurement unit; and a control system for operating the electrodes and for analyzing the electrical output. The invented technique for monitoring hemodynamic parameters is principally different from the existing systems in that the invented system includes a two-component (volumetric and velocimetric) approach providing a selective use of either one of the $\Delta R$ and dR/dt data, or possibly both of them, where $\Delta R \cdot (\alpha+\beta)/\beta$ and dR/dt·T are used interchangeably. The use of this novel approach preferably introduces a hydration factor for correction of $\Delta R$ value.

The invention also provides for determining the hydration status of a patient by measuring the resistivity of the regional part of a patients body and deriving the patients hydration status. Optionally, the resistivity of the interstitial fluid in the body is measured to derive the patient's hydration status. The patient's hydration state influences the amplitude and shape of the impedance waveform, as described above.

As indicated above, the measurement/monitoring system of the present invention may be configured as a tetrapolar or bipolar electrical integral bioimpedance measurement system for measuring cardiovascular parameters. The tetrapolar mode is more accurate compared to the bipolar mode, because it excludes the influence of impedance between an electrode and a patient's skin. This impedance $Z_{skin}$ does not provide any useful information about the cardiovascular parameters of a patient; $Z_{skin}$ is an interference to body impedance and is influenced by the condition of the patient's skin (whether it is oily or dry, etc.).

Figure 3A:
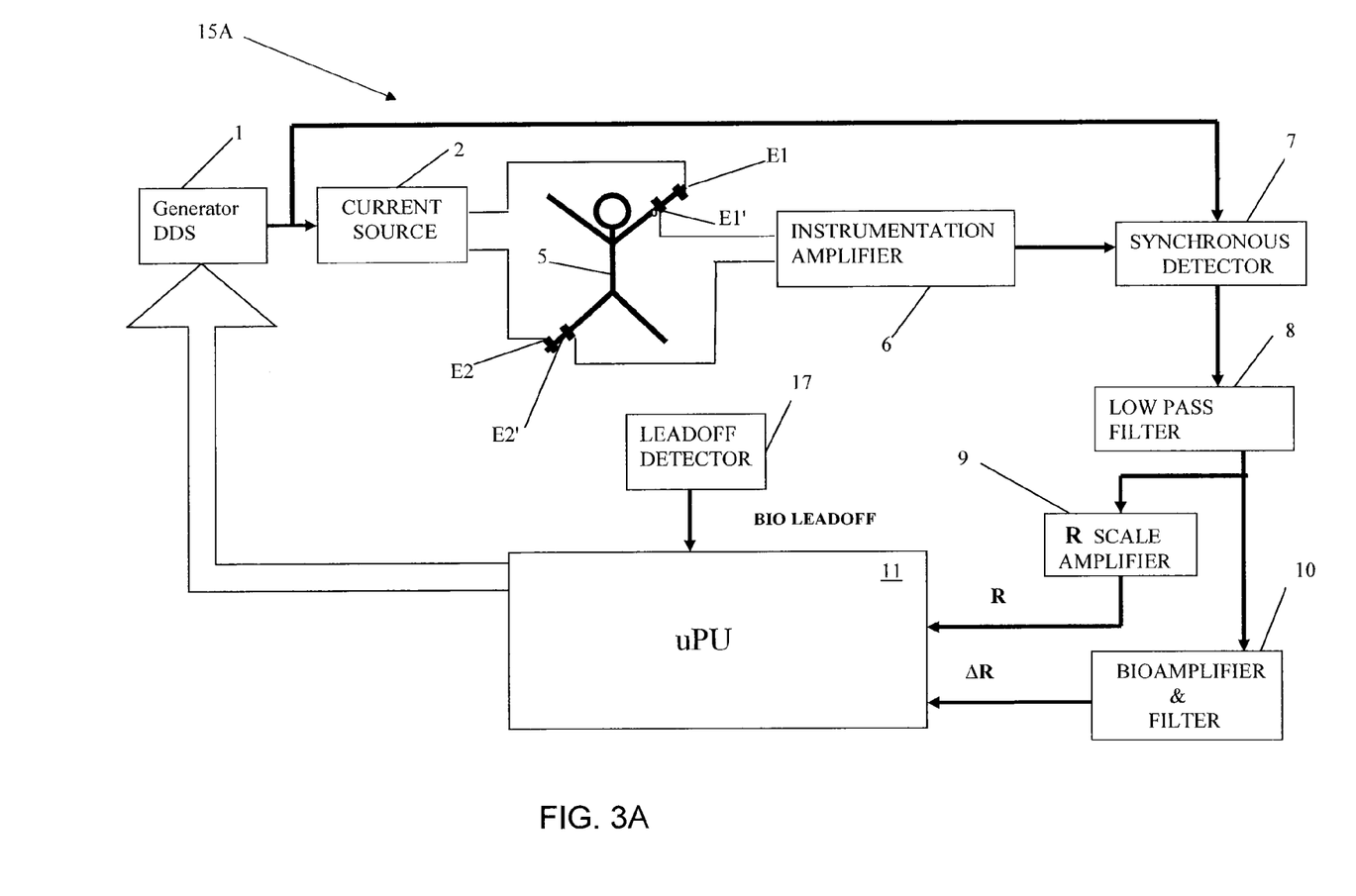
FIGS. 3A and 3B are block diagrams showing more specifically two examples, respectively, of the configuration of the measuring system according to the invention.

Reference is made to FIG. 3A showing one specific but not limiting example of the configuration of the measurement unit, generally at 15A, of the present invention. It should first be noted that a human body behaves, from an electrical point of view, as a resistance-capacitance (RC) impedance. The value of impedance is influenced by the injection current frequency. This frequency is about 32 KHz. The frequency of injecting current is controlled by a direct digital syntheser (DDS) generator 1 (which is a part of the measurement unit 15A in FIG. 1A), which is in turn operated by a microcontroller 11. The output frequency and amplitude of a sinusoidal signal are controlled to be stable. This signal operates a current source 2 (at the measurement unit 15A). The current source produces an electric current of the high-stability amplitude which is applied through two electrodes $E_1$ and $E_2$ at locations 3 and 4, respectively, to a patient's body 5. Also preferably provided in the measurement unit is a leadoff detector 17, which is used to sense the absence of a contact between the electrode and the body.

The read voltage signal, proportional to the human body impedance Z (i.e. an integral bioimpedance), is transferred from two voltage electrodes $E'_1$ and $E'_2$ at locations $3a$ and $4a$ respectively (+V, −V) to a high precision instrumentation amplifier 6, the output of which is fed to the first input of a synchronous detector 7. The latter has two functions: (1) it rectifies the obtained integral bioimpedance signal; and (2) it provides simultaneous derivation of the active component R of the integral bioimpedance signal vector. This component is directly proportional to the resistive component of the lead (resistance of the blood system). Linearity of the synchronous detector 7 simplifies the calibration process and reduces it to a single-step initial adjustment (instead of a per cycle calibration).

The output of detector 7 is connected to a low frequency filter 8 which may for example be a low pass Bessel filter. Filter 8 cuts off high frequency components, for example above 32 KHz, and delivers an operating signal, which has the active bioimpedance component (DC) R, and the waveform bioimpedance signal (AC) ΔR. The operating signal is input to R Scale Amplifier 9 and to Bioamplifier and Filter 10. Amplifier 9 produces an output signal proportional to the active bioimpedance component R and transmits the same to an input ADC (Analog-to-Digital Converter) of the microcontroller 11. Bioamplifier and Filter 10 separates from the operating signal the waveform ΔR component. The output of the Bioamplifier and Filter 10 is connected to another input ADC of microcontroller 11. The latter communicates with a HOST processor (data processing and analyzing utility 18B of control system 18 in FIG. 1A) which is not shown here.

Figure 3B:
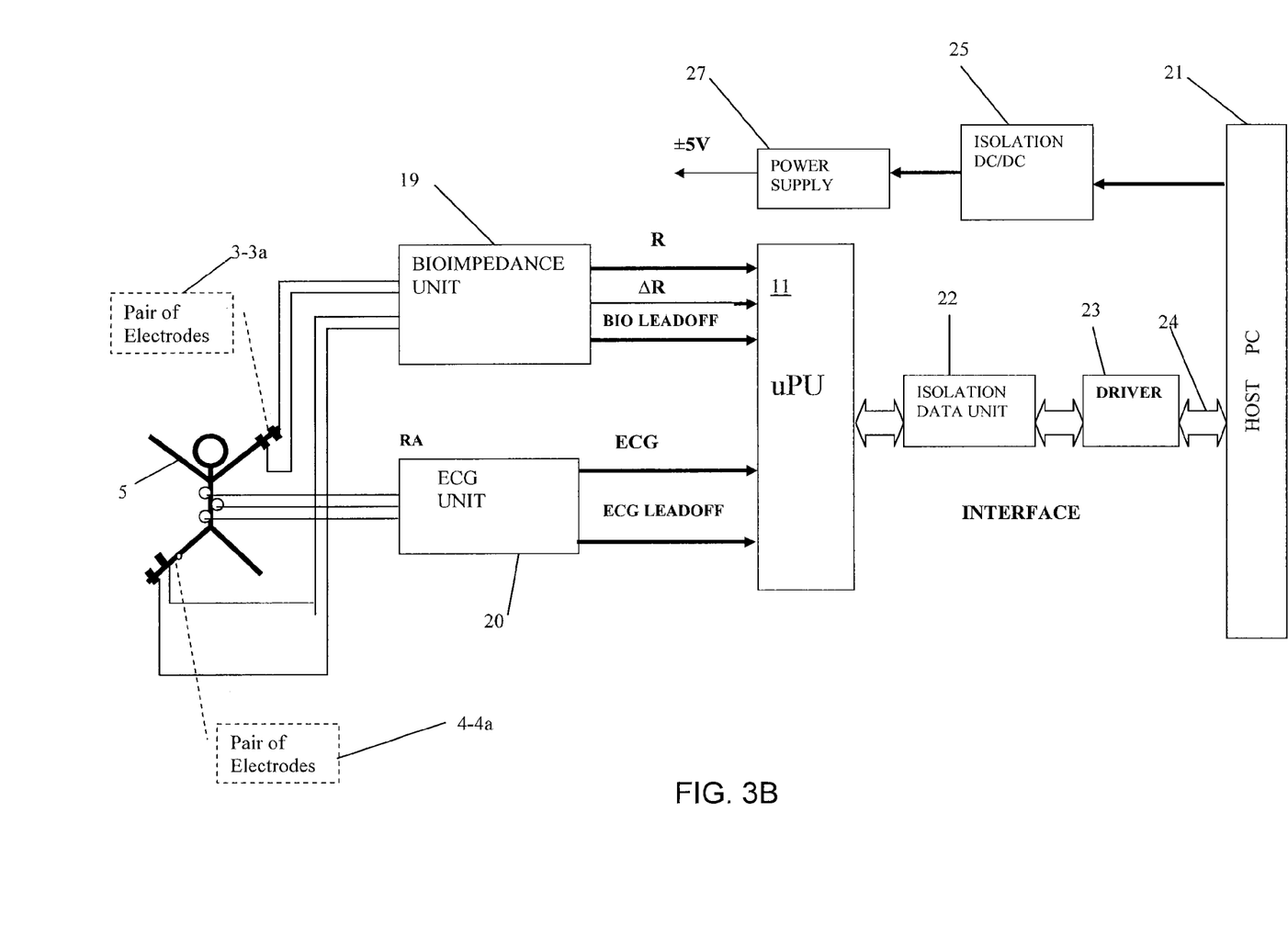

FIG. 3B further exemplifies the configuration of the measurement system of the invention. Here, three additional ECG electrodes are used being applied to the chest of a patient and connected to an ECG measurement circuit 20. The measurement system includes a measurement unit (15A in FIG. 1A) and a control system (18 in FIG. 1A). The latter is represented in FIG. 3B by a HOST processor 21. The measurement unit includes a bioimpedance signal receiver unit 19 and a microcontroller 11 (such as model ADuC814 commercially available from Analog Device®), which combines the functions of an A/D converter and a microprocessor, and operates for real time processing of first data or curve (which is a composition of direct "R" and alternating "ΔR" components of an active bioimpedance signal obtained from the bioimpedance receiver unit 19, together with second data (curve) obtained from the ECG circuit 20. Additionally, microcontroller 11 preferably also receives data indicative of the detected leadoff condition with regard to all the electrodes including those of the bioimpedance measuring unit 15A (bio leadoff) and those of the ECG measurement circuit (ECG leadoff).

The outputs of microcontroller 11 are connected to HOST processor 21 of the control system via an isolation data unit 22 (such as opto-isolators HCPL2611HP®) providing electrical protection of the patient from high voltage, via a Driver circuit 23 (such as the driver RS232C or USB) and interface utility 24 (via wires or wireless). The entire system is power supplied (e.g. +5V) from the host processor via an isolating DC/DC circuit 25 and further a power supply unit 27 which stabilizes the voltage value.

Figure 4A:
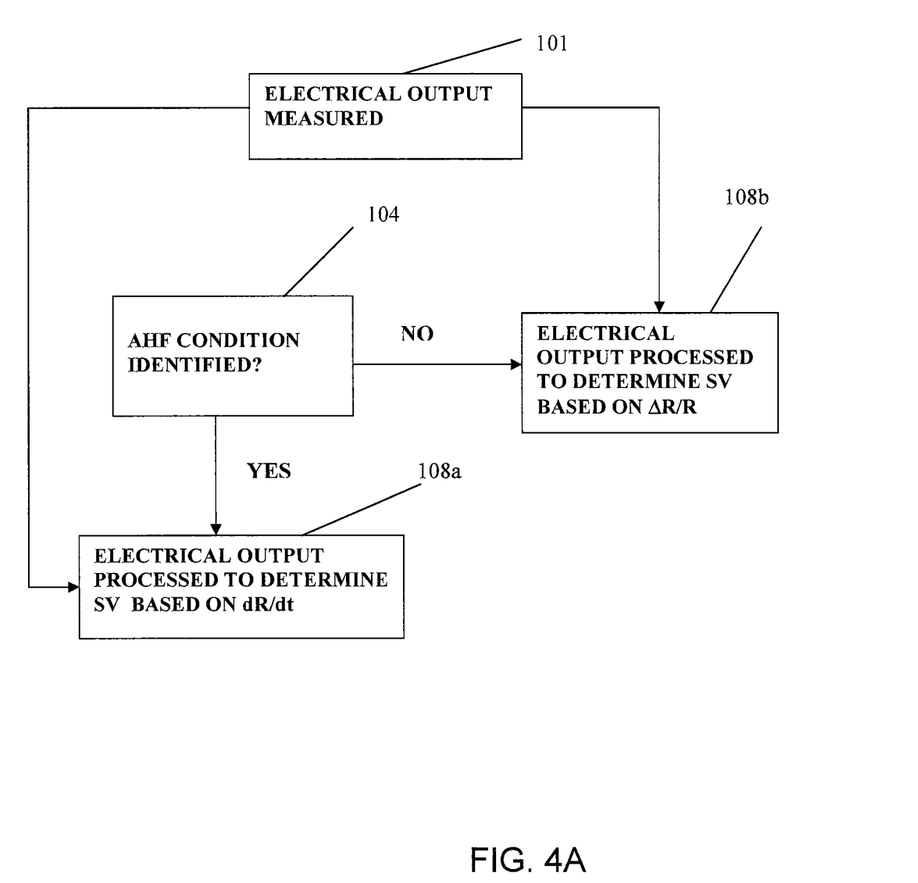
FIGS. 4A to 4C show three examples, respectively, of a method according to the invention for determining the patient's stroke volume.
Figure 4B:
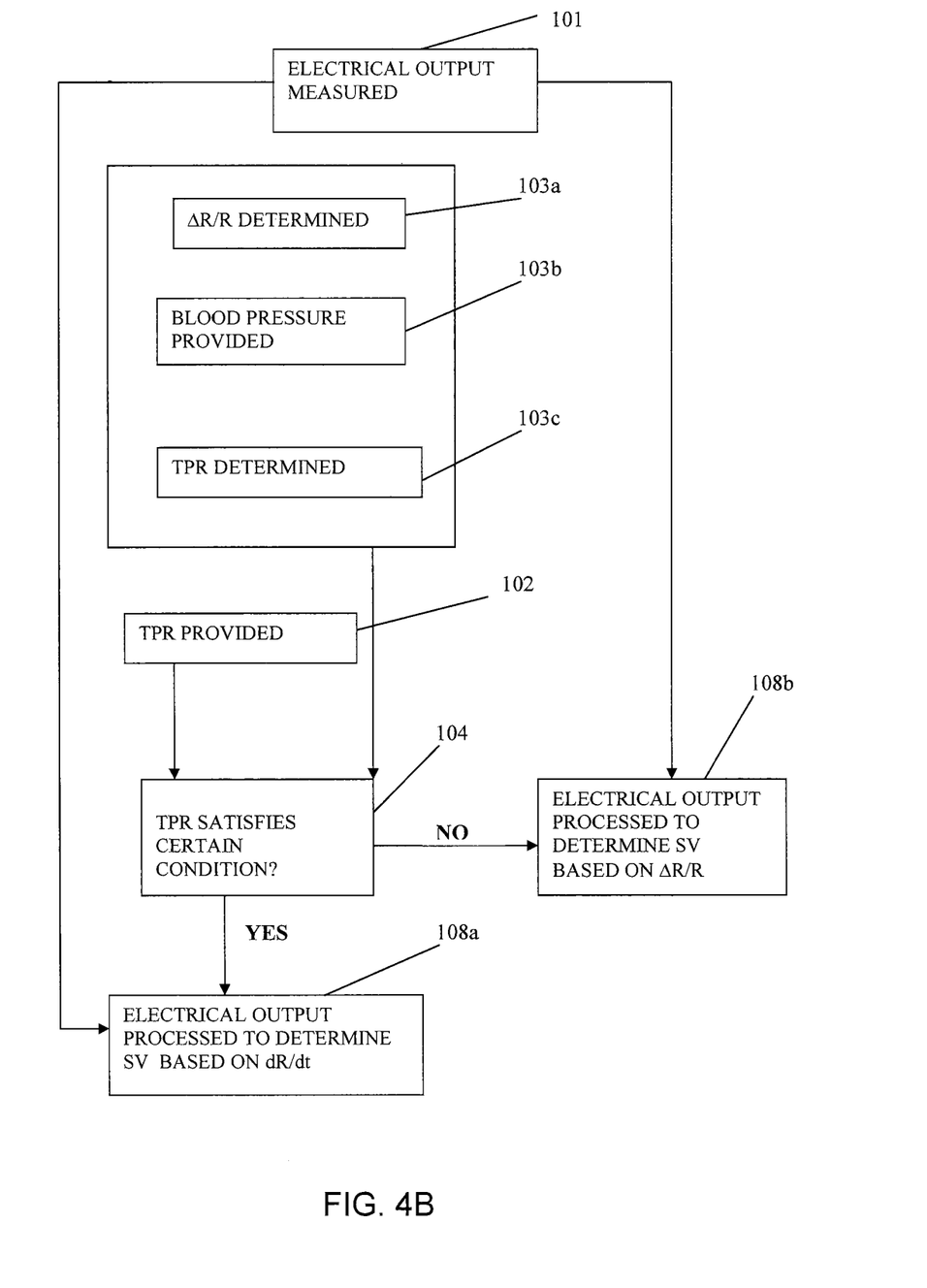
Figure 4C:
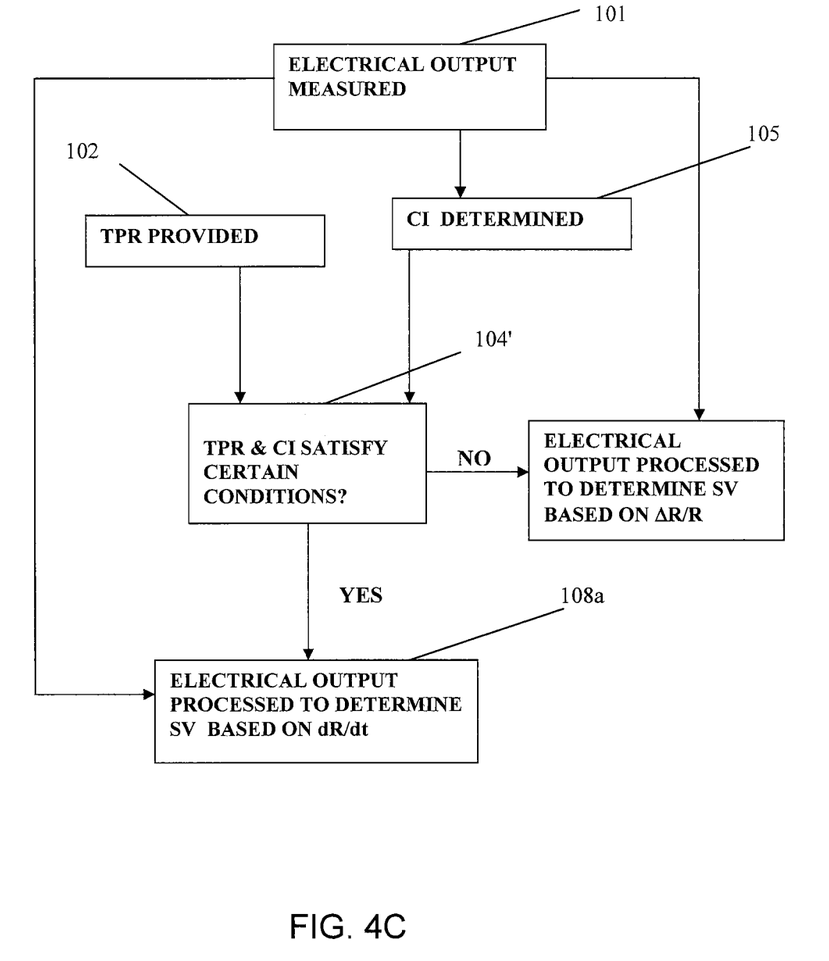

Reference is made to FIGS. 4A to 4C exemplifying a method of the present invention for determining a patient's stroke volume. To facilitate understanding, the same reference numbers are used for identifying the common steps in the flow charts of FIGS. 4A-4C.

Measurements are taken on the patient using the electrodes' arrangement (of either one of FIGS. 1A and 2A) to obtain the electrical output (step 101).

In the example of FIG. 4A, additionally, the patient's heart condition is analyzed to identify whether the acute heart failure (AHF) condition exists or not (step 104). If this condition exists, then the electrical output data is processed (at the HOST processor) to determine the SV value based on the dR/dt function (step 108a), and if the condition is not identified the HOST processor operates to process the electrical output data to determine the SV value based on the dR/R function (step 108b). As indicated above, this selective processing includes using either one of formulas (1)-(3) or setting the coefficients $k_{dr}$ and $k_{HR}$ in formula (5) for the ΔR/R function based measurements; or using formula (4a) or (4b) or setting the coefficients $k_{dr}$ and $k_{HR}$ in formula (5) for the dR/dt function based measurements.

In the example of FIG. 4B, data indicative of the patient's TPR is provided (step 102). As shown in the figure, this data may be independently provided (step 102). Preferably, as shown in the figure, this data may be obtained by calculation: using the cardiac output dR/R form the same measured data indicative of the electrical output (step 103a) and a separate measurement of the patient's blood pressure (step 103b) and calculating the TPR being a function of these two parameters (step 103c). Then, the TPR data is analyzed at the HOST processor (step 104) to determine whether the TPR value satisfies a first predetermined condition, to apply selective processing to the electrical output data. This condition sets the TPR value to be about 30% higher than the top limit of the normal range (which is about 750-1500 dynes·sec·cm$^{-5}$), e.g. TPR being above a certain value within a range from about 1800 dynes/sec$^{-5}$ to about 1900 dynes/sec$^{-5}$, e.g. being above 1800. If this condition is satisfied, then the electrical output data is processed (at the HOST processor) to determine the SV value based on the dR/dt function (step 108a), and if the condition is not satisfied the HOST processor operates to process the electrical output data to determine the SV value based on the dR/R function (step 108b). As indicated above, this selective processing includes using either one of formulas (1)-(3) or setting the coefficients $k_{dr}$ and $k_{HR}$ in formula (5) for the dR/R function based measurements; or using formula (4a) or (4b) or setting the coefficients $k_{dr}$ and $k_{HR}$ in formula (5) for the dR/dt function based measurements.

FIG. 4C shows yet another example of a method of the present invention. The example of FIG. 4C differs from the previous examples in that the selective processing is based, additionally or alternatively to the examples of FIGS. 4A and 4B, on determination of a cardiac index CI (step 105), derived from the measured cardiac output as CI=(ΔR/R)/BSA, BSA being the body surface area, and analyzing whether the cardiac index CI satisfies a second predetermined condition, which is used alternatively or additionally to the analysis of the TPR value (step 104'). According to this second condition, the CI is below 2.5 lit/min/m². If this condition is satisfied (alone or together with the above-described first condition), the electrical output data is processed to determine the SV value based on the dR/dt function (step 108a), and if the condition is not satisfied, the electrical output data is processed to determine the SV value based on the ΔR/R function (step 108b).

The following are some examples of the experimental data showing the features of the present invention:

Tables 1 and 2 below show the SV measurement results of 16 patients, AS23-AS38, with acute heart failure (group A) and of 29 ICU patients WS26-WS54 after coronary surgery (group B) by volumetric and by velocimetric approaches as compared with their concomitant thermodilution (TD) SV results.

TABLE 1

| Pt No | Sex | Age | Cardiac Index lit/min/m² TD | NIC | SV TD Cc | SV ΔR cc | Diff % ΔR vs TD | SV dR/dt cc | Diff % dR/dt vs TD | TPR (dyne · sec · cm⁻⁵) |
|---|---|---|---|---|---|---|---|---|---|---|
| AS 23 | F | 65 | 3.3 | 3.8 | 68 | 76 | +12 | 64 | −6 | 1607 |
| AS 24 | F | 90 | 1.8 | 1.8 | 38 | 38 | 0 | 41 | +8 | 4026 |
| AS 25 | M | 60 | 2.3 | 2.4 | 59 | 60 | +1.7 | 79 | +34 | 1857 |
| AS 26 | M | 78 | 1.1 | 0.6 | 24 | 16 | −33 | 26 | +8 | 2100 |
| AS 27 | M | 74 | 1.9 | 1.9 | 46 | 54 | +17 | 43 | −7 | 1890 |
| AS 28 | M | 66 | 2.0 | 1.9 | 78 | 74 | −5 | 79 | +1 | 2455 |
| AS 29 | F | 66 | 2.2 | 2.6 | 54 | 63 | +17 | 64 | +18 | 1527 |
| AS 30 | M | 66 | 2.7 | 2.8 | 60 | 54 | −10 | 55 | −8 | 1485 |
| AS 31 | M | 67 | 2.7 | 2.2 | 69 | 53 | −23 | 72 | +4 | 1900 |
| AS 32 | M | 62 | 1.7 | 1.2 | 62 | 47 | −24 | 68 | +10 | 4561 |
| AS 33 | F | 76 | 3.0 | 3.0 | 98 | 90 | −8 | 109 | +11 | 1741 |
| AS 34 | M | 79 | 2.2 | 2.6 | 51 | 64 | +25 | 61 | +20 | 1826 |
| AS 35 | F | 75 | 2.5 | 3.3 | 66 | 64 | −3 | 66 | 0 | 1550 |
| AS 36 | M | 89 | 1.7 | 1.3 | 48 | 35 | −27 | 40 | −17 | 3806 |
| AS 37 | M | 86 | 1.4 | 1.0 | 32 | 25 | −22 | 30 | −6 | 2900 |
| AS 38 | F | 70 | 2.2 | 1.8 | 44 | 38 | −14 | 38 | −14 | 2586 |

TABLE 2

| Pt No | Sex | Age | Cardiac Index lit/min/m² TD CI | NI CI | SV TD cc | SV ΔR cc | Diff % ΔR vs TD | SV dR/dt | Diff % dR/dt vs TD | TPR (dyne · sec · cm⁻⁵) |
|---|---|---|---|---|---|---|---|---|---|---|
| WS 26 | F | 74 | 5.4 | 5.6 | 106 | 117 | +10 | 89 | −16 | 706 |
| WS 27 | F | 67 | 2.1 | 1.8 | 43 | 37 | −14 | 44 | +2 | 2510 |
| WS 28 | M | 79 | 2.6 | 2.4 | 56 | 56 | 0 | 54 | −4 | 1505 |
| WS 29 | M | 70 | 2.2 | 2.4 | 39 | 39 | 0 | 36 | −8 | 1625 |
| WS 30 | M | 52 | 4.4 | 3 | 64 | 54 | −16 | 64 | 0 | 1001 |
| WS 31 | M | 70 | 4.2 | 4.4 | 58 | 70 | +21 | 67 | +16 | 1163 |
| WS 32 | F | 88 | 1.6 | 1.5 | 35 | 31 | −11 | 35 | 0 | 4164 |
| WS 33 | F | 74 | 2.6 | 2.8 | 42 | 50 | +19 | 48 | +14 | 1926 |
| WS 34 | M | 60 | 2.2 | 2.4 | 52 | 52 | 0 | 47 | −10 | 1805 |
| WS 35 | M | 54 | 3.3 | 3.6 | 59 | 62 | +5 | 54 | −9 | 1142 |
| WS 36 | M | 62 | 3.7 | 3.9 | 88 | 77 | −12 | 73 | −17 | 1151 |
| WS 37 | M | 55 | 3.3 | 3.3 | 68 | 65 | −4 | 55 | −19 | 906 |
| WS 38 | M | 72 | 2.2 | 2.4 | 59 | 54 | −8 | 59 | 0 | 1696 |
| WS 39 | M | 65 | 2.9 | 2.9 | 55 | 53 | −4 | 55 | 0 | 1031 |
| WS 40 | M | 76 | 2.2 | 2.3 | 39 | 37 | −5 | 42 | +8 | 1376 |
| WS 41 | M | 57 | 3.8 | 4.1 | 80 | 74 | −7 | 85 | +6 | 746 |
| WS 42 | F | 75 | 3.1 | 3.2 | 48 | 50 | +4 | 52 | +8 | 1475 |
| WS 43 | F | 79 | 2.5 | 2.5 | 56 | 56 | 0 | 58 | +4 | 1499 |
| WS 44 | M | 53 | 4.6 | 4.5 | 85 | 79 | −7 | 71 | −16 | 711 |
| WS 45 | F | 76 | 1.8 | 1.9 | 36 | 37 | +3 | 44 | +22 | 1436 |
| WS 46 | M | 62 | 3.8 | 4 | 54 | 54 | 0 | 53 | −2 | 897 |
| WS 47 | M | 68 | 4.3 | 4.2 | 85 | 73 | −14 | 98 | +15 | 900 |
| WS 48 | M | 55 | 3.1 | 3 | 58 | 57 | −2 | 67 | +15 | 1571 |
| WS 49 | M | 88 | 3.3 | 3 | 68 | 64 | −6 | 73 | +7 | 1509 |

TABLE 2-continued

| Pt No | Sex | Age | Cardiac Index lit/min/m² TD CI | NI CI | SV TD cc | SV ΔR cc | Diff % ΔR vs TD | SV dR/dt | Diff % dR/dt vs TD | TPR (dyne · sec · cm⁻⁵) |
|---|---|---|---|---|---|---|---|---|---|---|
| WS 50 | F | 75 | 2.7 | 3 | 63 | 70 | +11 | 66 | +5 | 1406 |
| WS 51 | M | 47 | 4.9 | 4.9 | 105 | 104 | −1 | 79 | −25 | 654 |
| WS 52 | M | 77 | 1.6 | 1.7 | 28 | 27 | −4 | 28 | 0 | 2662 |
| WS 53 | F | 64 | 1.9 | 1.8 | 35 | 36 | +3 | 32 | −9 | 2251 |
| WS 54 | F | 54 | 3.7 | 3.8 | 71 | 68 | −4 | 78 | +10 | 1313 |

When in group A (Table 1) the total peripheral resistance (TPR) was equal or higher than 1900 dyne·sec·cm⁻⁵, the ΔR-based SV results were significantly underestimated (lower by 18% versus TD), whereas the dR/dt-based results were in good agreement with TD values. However, in group A, where TPR was lower than 1900 dyne·sec·cm⁵, as well as in the entire group B, ΔR- and dR/dt-based results were in good accordance with the thermodilution SV results. It is thus evident that in acute heart failure, measuring the SV is substantially more reliable by the peripheral velocimetric rather than by the volumetric ICG formula. This is in contrast to post-open-heart ICU results, where the volumetric formula performs better. While the present invention has been described with the reference to the attached drawings, it should be appreciated, that other embodiments of the described system and its elements can be suggested and should be considered as part of the invention.

The invention claimed is:

1. An impedance measurement system for assessment of at least one cardiac parameter of an individual, the impedance measurement system comprising:

a measurement unit comprising an electrodes arrangement comprising a first and second electrode sets, the first electrode set being configured and operable to attach to one arm at a first lateral side of the individual's body and the second electrode set being configured and operable to attach to one leg at a second lateral side of the individual's body, said electrodes arrangement being configured and operable to apply an electrical field to the body through one of the first and second electrode sets and to obtain an electrical output through the other of the first and second electrode sets, said electrical output comprising measured data indicative of both systolic impedance change, ΔR, and velocity of a systolic impedance change, δR/δt, of the individual during a cardiac cycle; and a control unit comprising:

a data input utility configured and operable for receiving input data indicative of at least one condition of the individual, said at least one condition being indicative of whether the individual is sustained by an acute heart failure (AHF), and for receiving said measured data;

a processor programmed for analyzing said input data indicative of said at least one condition of the individual, and upon identifying that said input data is indicative of that the individual is sustained by AHF, selecting the data of the velocity of systolic impedance change for calculating the at least one cardiac parameter of the individual, and upon identifying that said input data is indicative of that the individual is not sustained by AHF, either selecting the data of systolic impedance change for calculating the at least one cardiac parameter, or analyzing additional input data indicative of at least one other predetermined condition of the individual in order to determine whether to use the systolic impedance change data or the velocity of systolic impedance change data, said at least one other condition comprising value of at least one of a total peripheral resistance (TPR) and a cardiac index (CI); and a data output utility configured and operable for generating an output indicative of the calculation result.

2. The computer system of claim 1, wherein said at least one cardiac parameter is selected from the following: stroke volume, cardiac output, cardiac index, stroke index, heart rate.

3. The computer system of claim 1, wherein said processor utilizes first measured data of the systolic impedance change and second measured data indicative of at least an individual's blood pressure; in order to determine the individual's TPR.

4. The computer system of claim 1, wherein said CI is determined as CI=CO/BSA, where BSA is the individual's body surface area, and CO is the individual's cardiac output determined from the measured data.

5. The computer system of claim 1, wherein said at least one other predetermined condition is satisfied when the measured TPR value is higher than a value ranging from 1800 dynes/sec⁻⁵ to 1900 dynes/sec⁻⁵.

6. The computer system of claim 1, wherein said at least one other predetermined condition is satisfied when the cardiac index is above 2.5.

7. The computer system of claim 1, wherein the calculation of said at least one cardiac parameter based solely on the systolic impedance change data is performed using the Frinerman formula:

$$SV = \frac{Hct_{corr.}}{K(\text{sex, age})} \cdot \frac{\Delta R}{R} \cdot \frac{H^2_{corr}}{R} \cdot \frac{\alpha + \beta}{\beta} \cdot K_{el} \cdot K_w \cdot IB$$

wherein: $Hct_{corr}$ is the correcting factor depending from Hematocrit; Hct is the Hematocrit; $K_{sex,\ age}$ is the coefficient of the individual's body depending on the sex and age of the individual; R is the basic resistance of the individual's body during one cardiocycle; $H^2_{corr}$ is the corrected height of the patient; $K_{el}$ is the coefficient of electrolytic ions in the individual's blood; $K_w$ is the weight coefficient for the corresponding sex and age of the individual; and IB is the index balance.

8. The computer system of claim 1, wherein the calculation of said at least one cardiac parameter based solely on the systolic impedance change data is performed using a formula $$SV = \frac{\Delta R \cdot \rho \cdot L^2 \cdot (\alpha + \beta) \cdot KW \cdot HF}{R \cdot R_i \cdot \beta}$$

wherein SV is the cardiac stroke volume (ml), ΔR is the blood resistance change (ohm) during the cardiac cycle, R is the basal resistance (ohm), $R_i$ is the corrected basal resistance (ohm), ρ is the specific resistivity of blood (ohm/cm), L is the individual's height (cm), KW is the corrected factor for the body weight, HF is the hydration factor related to the body's water composition, (α+β)/β is the ratio between the systolic and diastolic time intervals α and β and the diastolic time β for the ΔR waveform.

9. The computer system of claim 1, wherein the calculation of said at least one cardiac parameter based solely on the systolic impedance change data is performed using a formula:

$$SV = \frac{\Delta R \cdot k_{HR} \cdot (\alpha + \beta)}{\beta} \cdot \rho \cdot \frac{L^2}{R \cdot R_i} \cdot KW \cdot HF$$

wherein SV is the cardiac stroke volume (ml), ΔR is the blood resistance change (ohm) during the cardiac cycle, R is the basal resistance (ohm), $R_i$ is the corrected basal resistance (ohm), ρ is the specific resistivity of blood (ohm/cm), L is the individual's height (cm), KW is the corrected factor for the body weight, HF is the hydration factor related to the body water composition, (α+β)/β is the ratio between the systolic and diastolic time intervals α and β and the diastolic time β for the ΔR waveform, and $k_{HR}$ is the heart rate coefficient for correction.

10. The computer system of claim 1, wherein the calculation of said at least one cardiac parameter based solely on said data of the velocity of the impedance change is performed using a formula:

$$SV = k_{dr} \cdot \frac{dR}{dt} \cdot T \cdot \rho \cdot \left(\frac{L}{R}\right)^2$$

wherein SV is the cardiac stroke volume (ml), dR/dt is the peak of the first derivative of the blood resistance change during the cardiac cycle (ohm/sec), R is the basal resistance (ohm), T is the cardiac ejection time (sec), L is the length between voltage pick-up electrodes, and $k_{dr}$ is a calibration factor.

11. The computer system of claim 1, wherein the calculation of said at least one cardiac parameter based solely on said data of the velocity of the impedance change is performed using a formula:

$$SV = k_{dr} \cdot \frac{dR}{dt} \cdot T \cdot \rho \cdot \frac{L^2}{R \cdot R_i} \cdot KW \cdot HF$$

wherein SV is the cardiac stroke volume (ml), dR/dt is the peak of the first derivative of the blood resistance change during the cardiac cycle (ohm/sec), R is the basal resistance (ohm), $R_i$ is the corrected basal resistance (ohm), ρ is the specific resistivity of blood (ohm/cm), T is the cardiac ejection time (sec), L is the length between voltage pick-up electrodes, KW is the corrected factor for the body weight, HF is the hydration factor related to the body water composition, and $k_{dr}$ is a calibration factor.

12. The computer system of claim 1, wherein said calculation of said at least one cardiac parameter based on either the systolic impedance change data or on said data of the velocity of the impedance change is performed by a two-part equation $$SV = \left[\frac{\Delta R \cdot k_{HR} \cdot (\alpha + \beta)}{\beta} + k_{dr} \cdot \frac{dR}{dt} \cdot T\right] \cdot \rho \cdot \frac{L^2}{R \cdot R_i} \cdot KW \cdot k_{HF}$$

wherein SV is the cardiac stroke volume (ml), ΔR is the blood systolic impedance change (ohm) during the cardiac cycle, dR/dt is the peak of the first derivative of the blood resistance change during the cardiac cycle (ohm/sec), R is measured basal resistance (ohm), $R_i$ is the corrected basal resistance (ohm), ρ is the specific resistivity of blood (ohm/cm), L is the individual's height (cm), KW is the corrected factor for the body weight, HF is the hydration factor related to the body water composition, (α+β)/β is the ratio between the systolic and diastolic time intervals α and β and the diastolic time β for the ΔR waveform, and $k_{dr}$ is a calibration factor, and $k_{HR}$ is the heart rate coefficient for correction, while the coefficients $k_{HR}$ and $k_{dr}$ are set to 0 and 1 respectively when said at least one of the first and second conditions is satisfied and set to 1 and 0 where said at least one condition is not satisfied.

13. The computer system of claim 12, wherein the processor is adapted to determine the TPR data by processing the first measured data of the systolic impedance change and second measured data indicative of at least an individual's blood pressure.

14. The computer system of claim 13, wherein the CI is determined by: CI=CO/BSA, where BSA is the individual's body surface area, and where CO is the individual's cardiac output determined from the measured data.

15. The computer system of claim 12, wherein said at least one other predetermined condition is satisfied when the measured TPR value is about 30% higher than a top limit of a normal range.

16. The computer system of claim 15, wherein said at least one other predetermined condition is satisfied when the measured TPR value exceeds a value in a range from about 1800 (dynes/cm$^{-5}$) to about 1900 (dynes/sec$^{-5}$).

17. The computer system of claim 12, wherein said at least one other predetermined condition is satisfied when the cardiac index is above 2.5.

18. The computer system of claim 1, wherein said data input utility is configured for communication with a measurement unit for receiving said measured data.

19. The computer system of claim 1, wherein the calculation of the at least one cardiac parameter takes into account the patient's heart rate.

20. The measurement system of claim 1, wherein each of said electrode sets comprises one electrode or a pair of electrodes, and wherein said electrode arrangement comprises an additional electrode for use in an ECG measurement.

* * * * *